United States Patent
Hu et al.

(10) Patent No.: US 7,547,354 B2
(45) Date of Patent: *Jun. 16, 2009

(54) AMMONIACAL BORATE AND ZINC COMPOSITIONS, AND METHODS FOR TREATING WOOD PRODUCTS

(75) Inventors: Yatao Hu, Malvern, PA (US); Neil T. Miller, King of Prussia, PA (US); David M. Schubert, Lone Tree, CO (US)

(73) Assignees: PQ Corporation, Berwyn, PA (US); U.S. Borax Inc., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/547,375

(22) PCT Filed: Mar. 31, 2005

(86) PCT No.: PCT/US2005/010792

§ 371 (c)(1),
(2), (4) Date: Oct. 17, 2007

(87) PCT Pub. No.: WO2005/096821

PCT Pub. Date: Oct. 29, 2005

(65) Prior Publication Data

US 2008/0166481 A1    Jul. 10, 2008

Related U.S. Application Data

(60) Provisional application No. 60/559,486, filed on Apr. 3, 2004.

(51) Int. Cl.
*A01N 59/14* (2006.01)
*A01N 59/16* (2006.01)

(52) U.S. Cl. ............... 106/18.3; 106/15.05; 106/18.13; 424/641; 424/658; 424/659; 424/660; 424/DIG. 10; 424/DIG. 11

(58) Field of Classification Search ............. 106/15.05, 106/18.12, 18.13, 18.3; 427/297, 394, 395, 427/397, 397.8, 440; 424/641, DIG. 11, 424/658, 659, 660, DIG. 10
See application file for complete search history.

(56) References Cited

U.S. PATENT DOCUMENTS

| 2,194,827 | A | | 3/1940 | Gordon |
| 3,974,318 | A | | 8/1976 | Lilla |
| 4,656,060 | A | * | 4/1987 | Krzyzewski ................ 427/397 |
| 4,731,265 | A | | 3/1988 | Hirao et al. |
| 4,857,365 | A | | 8/1989 | Hirao et al. |
| 5,207,823 | A | * | 5/1993 | Shiozawa ................ 106/18.13 |
| 5,478,598 | A | * | 12/1995 | Shiozawa .................... 427/297 |
| 6,303,234 | B1 | | 10/2001 | Slimak et al. |
| 6,896,908 | B2 | * | 5/2005 | Lloyd et al. .................. 424/635 |
| 2003/0104135 | A1 | | 6/2003 | Grantham et al. |
| 2008/0069978 | A1 | | 3/2008 | Lenox et al. |
| 2008/0124478 | A1 | | 5/2008 | Hu et al. |

FOREIGN PATENT DOCUMENTS

| JP | 56-25363 | A | | 6/1980 |
| JP | 06336408 | A2 | | 12/1994 |
| JP | 1995251403 | A | | 10/1995 |
| JP | 2000-108108 | A | * | 4/2000 |
| WO | WO 01/70472 | A1 | | 9/2001 |
| WO | WO 2005/094586 | | | 10/2005 |
| WO | WO 2005/096822 | | | 10/2005 |

OTHER PUBLICATIONS

Dev, Indra et al., "Terminte resistance and permanency tests on zinc-borate—an environmental friendly preservative", J. Timb. Dev. Assoc. (India), vol. XLIII, No. 2, Apr. 1997.

* cited by examiner

*Primary Examiner*—Anthony J Green
(74) *Attorney, Agent, or Firm*—Kurt R. Ganderup

(57) ABSTRACT

Compositions and methods are provided for treating wood products to provide leach-resistant protection against fungal decay, termites and other wood destroying organisms. The preservative compositions provided include ammonia-stabilized solutions of zinc and boron, preferably in a molar ratio of Zn:B of between about 0.4:1 and 5:1, and are essentially copper free. The preservative may be applied by vacuum and/or pressure treatment or dip treatment under atmospheric pressure.

3 Claims, No Drawings

AMMONIACAL BORATE AND ZINC COMPOSITIONS, AND METHODS FOR TREATING WOOD PRODUCTS

This application is the national stage of International Application No. PCT/US2005/010792 filed on Mar. 31, 2005, which claims the benefit of U.S. Provisional Application No. 60/559,486, filed on Apr. 3, 2004, the entire contents of which are incorporated herein by reference.

FIELD OF THE INVENTION

This invention relates to the preservation of wood and more particularly, the invention provides compositions and methods for treating wood and wood products to provide leach-resistant protection against insect and fungal attack, as well as resistance to fire.

BACKGROUND OF THE INVENTION

Inorganic borate compounds have been used as wood preservatives for many years for protection against termites and other wood destroying insects, as well as fungal decay. Soluble borates such as borax, boric acid and disodium octaborate tetrahydrate are well known preservatives in aqueous-based systems for treating solid wood for use in protected environments. However, due to their water solubility they are readily leached from treated wood in exposed environments such as exterior and ground contact applications.

Copper chrome arsenate (CCA) is a leach-resistant wood preservative which has been used for may years to treat solid wood for use in exterior applications. However, due to environmental health and safety issues, and toxicity concerns relating to the constituent metals, particularly arsenic, CCA has come under increasing regulatory pressure and is being phased out of use in many areas. Even compositions containing copper without chromium or arsenic are coming into disfavor for environmental reasons, and thus it is desirable to reduce or eliminate copper content as well.

Solid zinc borate has proven very useful as a preservative for wood composites, where it is added as a solid material during manufacture of the composites. The inherent low solubility of zinc borate makes it resistant to leaching, even in high moisture environments. However, in view of its low solubility, it is not so easy to treat solid lumber with zinc borate. Dev et al. (*J. Timb. Dev. Assoc.*, 1997) describes a two-stage process for treating solid wood with zinc borate which involved impregnating the wood with solutions of borax and zinc in two separate steps. Ammonia-based solutions have been proposed to solubilize metals such as zinc and copper in an attempt to fix borates in wood. U.S. Pat. No. 2,194,827 (Gordon) discloses an aqueous ammonia solution of copper, zinc and borate salts for the treatment of wood.

SUMMARY OF THE INVENTION

In one aspect, the invention provides an aqueous preservative composition comprising a source of zinc selected from the group consisting of zinc oxide and soluble zinc salts; a source of borate selected from the group consisting of zinc borate, boric acid, boric oxide and water soluble borate salts; a source of ammonia; and water; wherein the composition is essentially copper-free and comprises at least 50 wt % water.

In another aspect, the invention provides an aqueous preservative composition consisting essentially of a source of zinc selected from the group consisting of zinc oxide and soluble zinc salts, a source of borate selected from the group consisting of zinc borate, boric acid, boric oxide and water soluble borate salts, a source of ammonia, and water, wherein the composition is essentially copper-free and comprises at least 50 wt % of water.

In yet another aspect, the invention provides a method of making an aqueous preservative composition comprising the steps of: (a) dissolving a source of zinc in an aqueous ammonia-containing solution to produce an aqueous zinc solution; (b) adding to the zinc solution a source of borate selected from the group consisting of zinc borate, boric acid, boric oxide and water soluble borate salts to the aqueous zinc solution; and (c) mixing until essentially all solids are dissolved, the composition being essentially copper-free.

In still another aspect, the invention provides a method for preserving an article comprising wood fibers, the method comprising the steps of:

(a) applying to the article an aqueous preservative composition prepared by combining ingredients comprising:
   i) a source of zinc selected from the group consisting of zinc oxide and soluble zinc salts;
   ii) a source of borate selected from the group consisting of zinc borate, boric acid, boric oxide and water soluble borate salts;
   iii) a source of ammonia; and
   iv) water;

such that the aqueous composition penetrates into the wood fibers, wherein the composition is essentially copper-free and comprises at least 50 wt % of water; and (b) drying the wood fibers such that there is deposited therein a bioeffective amount of a residual component comprising zinc and boron.

In a further aspect, the invention provides an article comprising wood fibers comprising a residual component comprising zinc and boron, prepared by treating the wood fibers according to the method set forth in the immediately preceding paragraph.

In a still further aspect, the invention provides a method for treating a substrate comprising wood fibers to provide resistance to flame spread, the method comprising the steps of:

(a) applying to the article an aqueous preservative composition prepared by combining ingredients comprising:
   i) a source of zinc selected from the group consisting of zinc oxide and soluble zinc salts;
   ii) a source of borate selected from the group consisting of zinc borate, boric acid, boric oxide and water soluble borate salts;
   iii) a source of ammonia; and
   iv) water;

such that the aqueous composition penetrates into the wood fibers, wherein the composition is essentially copper-free and comprises at least 50 wt % of water; and (b) drying the wood fibers such that there is deposited therein a flame retardant amount of a residual component comprising zinc and boron.

DETAILED DESCRIPTION OF THE INVENTION

The invention provides compositions for preservative treatment of items comprising wood or wood pulp, using an aqueous preservative composition solution comprising an ammonia-stabilized aqueous solution comprising zinc and borate. The preservative compositions are useful in the treatment of such items to provide borate leach-resistant protection against wood destroying organisms such as termites or other wood destroying insects, and decay fungi. The compositions may also provide other benefits to items with which they are treated, including resistance to fire. They are essentially copper free, by which it is meant that copper, if present at all, is present only as an impurity in the compositions of this invention, and is not purposely added. In any case, the compositions of the invention contain less than 0.1% copper by weight.

As used herein, the term "residual component" refers to a material comprising zinc and boron that remains in an article after being contacted with a composition according to the invention. It will be understood that the residual component may vary in composition according to the exact ratio and identity of the zinc and source of borates used in the treatment composition, as well as the amount and type of other materials that may be included in the composition.

As used herein, the term "bioeffective amount" as applied to a residual component means an amount of material sufficient to reduce or eliminate attack or residence on a treated article by one or both of an insect and a fungus that causes rot. Such reduction or elimination may be by any means, including but not limited to repelling, killing, and prevention of growth on or in the treated article.

As used herein, the term "flame retardant amount" as applied to a residual component means an amount of material sufficient to reduce or eliminate flame spread on a treated article.

As used herein, the term "essentially chloride ion free" means that none of the ingredients comprises chloride ion, other than as an impurity. In any case, a composition that is "essentially chloride free" contains less than 0.1% chlorine by weight.

As used herein, the term "sodium borate" means one or more of disodium octaborate tetrahydrate, sodium tetraborate decahydrate (borax), sodium tetraborate pentahydrate, sodium tetraborate (anhydrous borax), sodium metaborate, sodium pentaborate, and mixtures of any of these. The term "water soluble borate salt" means any sodium borate, any analogous potassium borate, any analogous ammonium borate, or mixtures of any of these.

References to amounts of ammonia or amines in a composition refer to the amount of that material calculated as its unbound form, although it will be understood that equilibrium processes may cause at least some of the compound to be in the form of a salt or other chemical species.

The preferred preservative concentrations for the preservative composition are between about 0.1 and 1 percent by weight boron (B), between about 0.2 and 4 percent by weight zinc (Zn) and between about 1 and 9 percent by weight ammonia ($NH_3$).

It has been found that higher molar Zn/B ratios reduce leaching of borate from treated substrates, provided that the resulting compositions do not suffer significant precipitation or gelation. Upper limits of Zn/B may however be imposed by practical considerations regarding stability of the formulation, and/or by precipitation or gelling reactions that occur due to the interaction of high concentrations of zinc with other ingredients. The preferred zinc to boron (Zn:B) mole ratio in the preservative composition is at least 0.4:1, typically at least 1:1, and more typically at least 1.5:1. The preferred ratio is at most 5:1, typically at most 3:1, and more typically at most 2:1. The preferred ammonia to zinc ($NH_3$:Zn) mole ratio in the preservative composition is in the range of about 7:1 to about 33:1. A ratio of about 10 is typical. Compositions according to the invention are aqueous mixtures containing at least 50 wt % water. The compositions typically contain at least 50 wt % water, but compositions having a higher concentration of active ingredients and a less than 50% water content may be used according to the invention. Such compositions may, for example, be kept as concentrates and diluted as needed prior to application. It has been found that choice of Zn:B and $NH_3$:Zn ratios within the ranges specified above, combined with the absolute concentration ranges set forth above, provides compositions having both good shelf life stability against gelling and precipitation and high resistance to leach-out of borate in items treated with the compositions.

Zinc Sources

Suitable sources of zinc for use according to the invention may be provided in the form of various zinc compounds including zinc oxide, zinc chloride, zinc acetate, zinc sulfate, and other water-soluble zinc salts. Other zinc salts such as zinc naphthenate, zinc acetylacetonate, zinc gluconate, and zinc complexes with chelating agents such as EDTA may also be used according to the invention. Alternatively, zinc borate may be used. In some embodiments of the invention, zinc chloride is a preferred source of zinc. In other embodiments, for example where it is desired to reduce the chloride ion content in the composition for purposes such as prevention of corrosion, zinc acetate or zinc sulfate may be preferred. Zinc serves to reduce the tendency of borate to leach from the wood upon exposure to water after it has been treated, possibly by formation of a zinc borate precipitate which is not readily soluble in water. Zinc may also contribute to the biocidal properties of the preservative compositions of the present invention. Ammonia, such as in the form of ammonium hydroxide ($NH_4OH$), aids the dissolution of zinc in the preservative composition.

Source of Borate

Suitable sources of borate for use according to the invention include boric acid and the water soluble salts thereof. Alternatively, zinc borate may be used. Preferred source of borates include the sodium borates, such as disodium octaborate tetrahydrate (commercially available as TIM-BOR® Industrial wood preservative manufactured by U.S. Borax Inc., Valencia, Calif.), sodium tetraborate decahydrate (borax), sodium tetraborate pentahydrate, anhydrous sodium tetraborate, sodium metaborate and sodium pentaborate, as well as other alkali metal borates and ammonium borates such as potassium tetraborate, potassium metaborate and ammonium pentaborate. Boric acid and boron oxide may also be used.

Source of Ammonia

Suitable sources of ammonia for use according to the invention may include, as nonlimiting examples, aqueous ammonium hydroxide and anhydrous ammonia.

Preparation of Preservative Compositions

The preservative compositions of the present invention are preferably prepared by dissolving a zinc compound in an aqueous ammonia solution, followed by the addition of a source of borate and agitating until essentially all solids are dissolved. The source of borate is preferably pre-dissolved in water prior to adding to the ammonia stabilized zinc solution. Vigorous mixing is recommended to promote the rapid dissolution of zinc and borate solid compounds in solution.

It has been found that mere dissolution of zinc borate in ammonia provides preservative compositions with poor borate leach performance; that is, wood treated with such compositions loses borate content when contacted with water over an extended period of time, as measured by test method AWPA E11-97. In contrast, wood that has been treated with compositions prepared according to the invention, especially those with higher Zn:B molar ratios, show notably lower borate leach rates, and therefore may be expected to retain their preservative activity for a longer time.

Wood Fibers

Wood fibers according to the invention may be fibers in a piece of wood, or fibers freed from wood by a pulping operation such as is commonly performed in the pulp and paper industry, i.e. wood pulp. As used herein, the term "wood" is to be understood according to its common use, and includes wood pieces or particles of any size or shape, including for example sawn lumber, plywood, oriented strand board, particle board, ground wood, sawdust, and wood/polymer composite materials. The term "wood" according to this use therefore refers to wood that has not been subjected to a pulping operation.

As used herein, the term "wood pulp" refers to wood that has been subjected to a pulping operation, including but not limited to Kraft pulping, sulfite pulping, and chemi-thermo-mechanical pulping. Wood pulp treated according to the invention may be in any form, including but not limited to unconsolidated (loose) pulp fibers, including for example blown insulation, and paper. Paper that comprises wood pulp treated according to the invention may be paper in any form, including but not limited to sheet paper, corrugated board, and paper comprising a surface of gypsum wallboard.

Application of the Preservative Composition

The preservative composition may be applied to the item to be treated by any commercially acceptable method, as long as sufficient composition penetrates into the item so as to result in the deposition of a bioeffective or fire retardant amount of a residual component. It should be noted that the residual component, which is the material that is active for deterrence of biological attack or attack by fire, may comprise zinc or borate in the form of the compounds that were used to prepare the composition. They may however represent the result of subsequent chemical reactions in the treated substrate. One possible nonlimiting example is formation of zinc borate in the treated article, but other chemical reactions may occur in addition or instead, or none may occur at all. Similarly, ammonia may be chemically bound in the treated item, or it may be essentially absent due to other chemical reactions or to volatilization out of the item. Regardless of the exact form and location of the zinc, borate, and ammonia after the treatment is complete, there remains a residual component that provides the preservative properties of the invention. Resistance to insects, wood-decay fungi, and/or fire is thereby achieved.

For wood products, application of the composition may involve a method such as vacuum and/or pressure treatment or dip treatment under atmospheric pressure. Preferably, treatment may involve both vacuum and pressure, wherein a vacuum is first applied to the wood product, prior to application of the preservative composition. The solution is then applied to the wood product and pressure is then applied to force the solution into the pores of the wood. Preferably, after the wood product has been treated, the treated wood may be dried to improve the leach resistant properties of the wood. Drying may be performed at an elevated temperature, preferably no higher than 90° C., even more preferably no higher than 70° C., with about 60° C. being typical. It has been found that the use of lower drying temperatures for a given amount of drying time tends to reduce the borate leach rate of items treated with these compositions. Thus in some embodiments of the invention, drying is performed under ambient temperatures, typically between about 20° C. and 25° C., optionally aided by the use of vacuum or blown air. Methods for drying wood, and the desired moisture level of dried wood, are well known in the art.

For applications in which resistance to biological attack is the desired result, it is believed that the amount of borate in the treated substrate should be at least 0.1%, measured as boric acid equivalents (BAE). A level of at least 0.5% will typically be used. In general, increased BAE provides increased resistance to biological activity, as well as to fire. Methods for applying the compositions include spraying, roll coating, dipping, and any other means known in the art relevant to the particular form of the wood or wood pulp.

EXAMPLES

Example 1

Five ammonia-stabilized zinc and borate-containing solutions, each having a zinc to boron (Zn:B) mole ratio of 0.4:1, were prepared according to the methods of the invention. The solution concentrations for the five solutions were designed to provide target retentions of about 0.13%, 0.25%, 0.50%, 0.75% and 1.5% $B_2O_3$ in the wood after treatment.

Sample $B_2O_3$ retention calculation:
Retention (%$B_2O_3$)=[(30g)(g $B_2O_3$/100 g treatment soln.)(62.4)]/[(100)(41.142 cc)] (This is a standard industry calculation, according to method AWPA E10-01, indicating the amount of boron (as $B_2O_3$) retained in a wood sample after treatment with a preservative composition.)

g $B_2O_3$/100 g treatment soln.=((Weight of Timbor, g)*(8 moles B/mole Timbor)*(69.62 g $B_2O_3$/mole $B_2O_3$)*(100 g treatment soln.))/((412.46 g Timbor/ mole Timbor)*(2 mole B/mole $B_2O_3$)*(400 g treatment soln.))

For 0.75% $B_2O_3$ solution:
a. g $B_2O_3$/100 g treatment soln.=(9.80*8*69.62*100)/(412.46*2*400)=1.654
b. Retention (%$B_2O_3$)=(30*1.654*62.4)/(100*41.142)=0.752

The amounts of each ingredient used in each of the five solutions, and the resulting concentrations of boron, zinc, and ammonia, are summarized in Table I. The method of preparation is described below, using the target 0.75% $B_2O_3$ solution as an example.

Ammonium hydroxide (69 mL of a 30% $NH_4OH$ solution) was stirred into 200.00 g of deionized water. Zinc chloride (10.36 g $ZnCl_2$) was added to the water-ammonia solution and the mixture was vigorously stirred until the zinc chloride was completely dissolved. In a separate container, 9.80 g of TIM-BOR® disodium octaborate tetrahydrate (manufactured by U.S. Borax Inc.) was dissolved in 110.89 g deionized water. The TIM-BOR® solution was then poured slowly with agitation into the zinc/ammonia solution, providing an essentially clear solution containing 0.51% B, 1.24% Zn, and 2.51% $NH_3$, thereby providing a composition having a Zn:B molar ratio of 0.4.

TABLE I

| | Target % $B_2O_3$ in Wood | | | | |
|---|---|---|---|---|---|
| | 0.13 | 0.25 | 0.50 | 0.75 | 1.50 |
| $H_2O$ (g) | 227.51 | 225.82 | 222.44 | 200.00 | 121.50 |
| 30% $NH_4OH$ (mL) | 50 | 50 | 50 | 69 | 137 |
| $ZnCl_2$ (g) | 1.80 | 3.49 | 6.87 | 10.36 | 20.62 |
| $H_2O$ (g) | 118.99 | 117.39 | 114.19 | 110.89 | 101.19 |
| TIM-BOR ® (g) | 1.70 | 3.30 | 6.50 | 9.80 | 19.50 |
| Wt. % Boron (B) | 0.09 | 0.17 | 0.34 | 0.51 | 1.02 |

TABLE I-continued

| | Target % $B_2O_3$ in Wood | | | | |
|---|---|---|---|---|---|
| | 0.13 | 0.25 | 0.50 | 0.75 | 1.50 |
| Wt. % Zinc (Zn) | 0.22 | 0.42 | 0.82 | 1.24 | 2.47 |
| Wt. % Ammonia ($NH_3$) | 1.82 | 1.82 | 1.82 | 2.51 | 4.99 |

Although no boron leaching experiments were performed on wood treated with the compositions of Table I, in general such results may be obtained by the following method. Cube-shaped wood blocks measuring 1.9 cm on each side and weighing between 3 and 5 g each (20 and 30 g total for 6 blocks) are vacuum-impregnated with the preservative compositions of Table I, using AWPA Method E11-97, "Standard Method of Determining the Leachability of Wood Preservatives." After treatment, the blocks are dried overnight at 60° C. and evaluated for degree of borate leaching according to Method E11-97.

Example 2

A zinc chloride/TIM-BOR® (disodium octaborate tetrahydrate) mixture (Zn:B=0.33) dissolved in ammonia, when applied to wood blocks as described in the preceding paragraph, resulted in loss of only 66% of the boron in 2 days of leaching. In contrast, wood blocks treated in the same manner, but using zinc borate (Zn:B=0.33) dissolved in ammonia, resulted in loss of 75% of the boron in 2 days of leaching.

Example 3

Three preservative compositions having a zinc to boron (Zn:B) mole ratio of 2:1 were prepared using the procedures described in Example 1. The three preservative compositions had the same boron concentrations as the first three compositions described in Table I. The solution concentrations for the three solutions were designed to provide target retentions of about 0.13%, 0.25%, and 0.50% $B_2O_3$ in the wood after treatment. The amounts of each component used in preparing each of the three solutions, along with the resulting solution concentrations are summarized in Table II.

TABLE II

| | Target % $B_2O_3$ in Wood | | |
|---|---|---|---|
| | 0.13 | 0.25 | 0.50 |
| $H_2O$ (g) | 239.23 | 176.51 | 45.00 |
| 30% $NH_4OH$ (mL) | 60 | 114 | 229 |
| $ZnCl_2$ (g) | 8.99 | 17.18 | 34.36 |
| $H_2O$ (g) | 90.28 | 88.73 | 85.48 |
| TIM-BOR ® (g) | 1.70 | 3.25 | 6.50 |
| Wt. % Boron (B) | 0.09 | 0.17 | 0.34 |
| Wt. % Zinc (Zn) | 1.08 | 2.06 | 4.12 |
| Wt. % Ammonia ($NH_3$) | 2.18 | 4.16 | 8.34 |

Wood blocks were impregnated with the compositions of Table II and evaluated according to the methods used in Example 2. The results for the run having a targeted 0.50% $B_2O_3$ in wood showed only a 27% and 56% boron leach after 2 and 14 days, respectively.

Example 4

Douglas fir whole wood samples were treated with a preservative composition according to this invention and subjected to cone calorimeter testing to evaluate fire retardancy. A preservative solution was made up by dissolving 3809 grams of Zinc chloride ($ZnCl_2$) and 719 grams of TIM-BOR™ disodium octaborate tetrahydrate in an aqueous ammonia solution comprising 26 liters of 30% $NH_4OH$ in 8381 grams of deionized water. Three wood samples, having an initial dry wood weight of 352.6 grams, were placed in a 7.5 inch inside diameter by 34 inch cylinder. A vacuum measured at 29 mm Hg was pulled on the cylinder containing the wood and held for 15 minutes. The valve leading to the tank containing the treating solution was opened and the treating solution was allowed to fill the cylinder until the pressure gauge registered 0 psi. The overflow valve was opened and treating solution was pumped into the cylinder until treating solution flowed out of the overflow valve. The overflow was closed and the cylinder was pressurized to 140 psi with treating solution. The cylinder was held at 140 psi liquid pressure for 30 minutes. The overflow valve was opened and pressure returned to atmospheric pressure for sample removal. The treated wood weighed 485.2 grams wet and 342.3 grams after being allowed to dry under ambient laboratory conditions. Therefore, the loading of the preservative composition in the wood was estimated to be 7%. The treated wood was then sent for cone calorimeter testing.

The cone calorimeter provides quantitative data on heat release, fire kinetics, and combustion gases for materials burning in the presence of a radiant heat source, including the following measurements: 1) time to ignition, 2) peak heat release rate, 3) time to peak rate of heat release, 4) three-minute heat release rate, 5) average heat release rate, 6) total heat release, and 7) afterglow time. All tests were conducted using a heat flux of 40 $kWm^{-2}$. Since moisture content can also greatly influence fire tests, all samples were conditioned prior to testing. Three treated wood samples and three untreated control samples were tested. Because wood is not a homogeneous material, a considerable amount of noise can be expected in test data. The cone calorimeter method is described in ASTM E 1354-02 and ISO 5660-1. The results of the calorimeter test are shown in Table III.

TABLE III

| Samples | Time to Ignition | Peak Heat Release Rate | Time to Peak Heat Release Rate | 3-Minute Peak Heat Release Rate | Average Heat Release Rate | Total Heat Release | Afterglow |
|---|---|---|---|---|---|---|---|
| Control 1 | 20 | 223.8 | 152 | 151.4 | 135 | 40.6 | 900 |
| Control 2 | 22 | 178.9 | 162 | 134 | 116.5 | 36.5 | 750 |
| Control 3 | 21 | 301.7 | 132 | 147.7 | 149.8 | 38.6 | 820 |

TABLE III-continued

| Samples | Time to Ignition | Peak Heat Release Rate | Time to Peak Heat Release Rate | 3-Minute Peak Heat Release Rate | Average Heat Release Rate | Total Heat Release | Afterglow |
|---|---|---|---|---|---|---|---|
| Ave. +/− stdev | 21 +/− 1 | 235 +/− 62 | 149 +/− 15 | 144.4 +/− 9.2 | 134 +/− 17 | 39 +/− 2 | 823 +/− 75 |
| Am/Zn 1 | 47 | 160.4 | 162 | 94 | 84.9 | 48.4 | >1440 |
| Am/Zn 2 | 42 | 198.7 | 144 | 92.5 | 95.1 | 43.6 | >1440 |
| Am/Zn 3 | 44 | 166.6 | 162 | 81.4 | 77.4 | 49.3 | >1440 |
| Ave. +/− stdev | 44 +/− 3 | 175 +/− 21 | 156 +/− 10 | 89.3 +/− 6.9 | 86 +/− 9 | 47 +/− 3 | >1440 |

Following is a brief analysis of the specific results:

Time to Ignition (Longer ignition times imply better fire performance)—The treated samples performed significantly better than the controls.

Peak Heat Release Rate (Lower PHRR values imply better fire performance)—The results for the control samples were rather erratic, however on average the treated samples performed substantially better.

Time to Peak Heat Release Rate (Longer times to PHRR imply better fire performance)—The treated samples performed slightly better, on average.

3-Minute Peak Heat Release Rate (Lower 3-Min PHRR implies better fire performance)—The treated samples performed significantly better than the controls.

Average Heat Release Rate (Lower AHRR values imply better fire performance)—The treated samples performed significantly better than the controls.

Total Heat Release (Lower THR values imply better fire performance)—The control samples performed better in this test.

Afterglow (Lower afterglow times imply better fire performance) The control samples performed better in this test.

In general, the treated samples consistently gave fire performance that was significantly better than the control samples, with the exception of the Total Heat Release and Afterglow.

The preservative solutions of this invention are suitable for treating wood products to provide leach-resistant protection against biological attack from a variety of wood-destroying organisms, including insects and fungal decay, as well as protection against fire. The compositions may be used alone, or they may be combined with other constituents or other compositions. Various changes and modifications of the invention can be made and to the extent that such changes and modifications incorporate the spirit of this invention, they are intended to be included within the scope of the appended claims.

What is claimed is:

1. An aqueous preservative composition consisting essentially of a source of zinc selected from the group consisting of zinc oxide and soluble zinc salts, a source of borate selected from the group consisting of zinc borate, boric acid, boric oxide and water soluble borate salts, a source of ammonia, and water, wherein the composition is essentially copper-free and comprises at least 50 wt % of water, and wherein the source of ammonia is ammonium hydroxide, the source of zinc is zinc chloride, and the source of borate is sodium borate.

2. An aqueous preservative composition consisting essentially of a source of zinc selected from the group consisting of zinc oxide and soluble zinc salts, a source of borate selected from the group consisting of zinc borate, boric acid, boric oxide and water soluble borate salts, a source of ammonia, and water, wherein the composition is essentially copper-free and comprises at least 50 wt % of water, and wherein the source of borate is disodium octaborate tetrahydrate.

3. An aqueous preservative composition consisting essentially of a source of zinc selected from the group consisting of zinc oxide and soluble zinc salts, a source of borate selected from the group consisting of zinc borate, boric acid, boric oxide and water soluble borate salts, a source of ammonia, and water, wherein the composition is essentially copper-free and comprises at least 50 wt % of water, from about 0.1 to about 1.0 weight percent boron, from about 0.2 to about 4 weight percent zinc, and from about 1 to about 9 weight percent ammonia.

* * * * *